United States Patent [19]

Smith et al.

[11] Patent Number: 5,519,534
[45] Date of Patent: May 21, 1996

[54] IRRADIANCE ATTACHMENT FOR AN OPTICAL FIBER TO PROVIDE A UNIFORM LEVEL OF ILLUMINATION ACROSS A PLANE

[75] Inventors: Paul D. Smith, Annapolis; John Cole, Potomac; Frank Harrington, Catonsville, all of Md.; Eric F. Bernstein, Wynnewood, Pa.

[73] Assignee: The Government of the United States of America as represented by the Secretary of the Department of Health and Human Services, Washington, D.C.

[21] Appl. No.: 248,918

[22] Filed: May 25, 1994

[51] Int. Cl.⁶ ............................... G02B 5/02; G01J 1/04; A61B 17/36; A61N 5/00
[52] U.S. Cl. ............. 359/599; 359/900; 250/228; 356/236; 385/31; 385/84; 606/16; 606/18; 607/88
[58] Field of Search ............................. 250/228; 356/236; 359/896, 579, 900; 385/31, 32, 77, 78, 79, 84; 606/2, 10, 15, 16, 17, 18, 19; 607/88, 89, 91, 92, 93

[56] References Cited

U.S. PATENT DOCUMENTS

| | | | |
|---|---|---|---|
| 2,342,771 | 2/1944 | Voigt | 356/236 |
| 3,847,024 | 11/1974 | Beever et al. | 356/236 |
| 3,874,799 | 4/1975 | Isaacs et al. | 356/236 |
| 3,968,363 | 7/1976 | Mielenz et al. | 250/228 |
| 4,580,557 | 4/1986 | Hertzmann . | |
| 4,583,860 | 4/1986 | Butner | 356/236 |
| 4,645,922 | 2/1987 | Welbourn et al. | 356/236 |
| 4,651,262 | 3/1987 | Piironen . | |
| 4,693,556 | 9/1987 | McCaughan, Jr. . | |
| 4,881,811 | 11/1989 | O'Brien | 356/236 |
| 4,883,333 | 11/1989 | Yanez . | |
| 4,889,129 | 12/1989 | Dougherty et al. . | |
| 4,950,059 | 8/1990 | Roberts . | |
| 4,986,628 | 1/1991 | Lozhenko et al. . | |
| 4,998,930 | 3/1991 | Lundahl | 606/15 |
| 5,047,006 | 9/1991 | Brandston et al. . | |
| 5,059,191 | 10/1991 | Beyer et al. . | |
| 5,133,709 | 7/1992 | Prince . | |
| 5,153,426 | 10/1992 | Konrad et al. | 250/228 |
| 5,212,448 | 5/1993 | Le Roux et al. . | |
| 5,225,780 | 7/1993 | Riederer et al. . | |
| 5,241,271 | 8/1993 | Taguchi et al. . | |
| 5,243,283 | 9/1993 | Tokunaga et al. . | |
| 5,251,004 | 10/1993 | Doiron et al. | 356/236 |
| 5,309,339 | 5/1994 | Webb . | |
| 5,344,419 | 9/1994 | Spears | 606/17 |
| 5,373,571 | 12/1994 | Reid et al. | 385/31 |

FOREIGN PATENT DOCUMENTS

| | | | |
|---|---|---|---|
| 2417399 | 10/1975 | Germany | 356/236 |
| 3327551 | 2/1985 | Germany | 356/236 |
| 0101714 | 5/1988 | Japan | 356/236 |
| WO90/00420 | 7/1989 | WIPO . | |

OTHER PUBLICATIONS

Berger et al; "Spectroscopy of Matrices and Thin Films with an Integrating Sphere", Applied Spectroscopy, vol. 43, No. 2, 1989 pp. 320–324.

Primary Examiner—Ricky D. Shafer
Attorney, Agent, or Firm—Lowe, Price, LeBlanc & Becker

[57] ABSTRACT

A irradiation attachment for an optical fiber which provides an output of light that has a highly uniform intensity. The device includes a hollow spherical shell having a diffusive reflective surface or target supported therein. Light is directed into the hollow spherical shell so that it reflects off the diffusive reflective surface or target. The reflected light is internally reflected off the inner surface of the hollow spherical shell several times before passing through an output aperture. As a result of the internal reflection within the hollow spherical shell, the light leaving the device has a highly uniform intensity. The device is particularly useful for photodynamic therapy.

18 Claims, 4 Drawing Sheets

IRRADIANCE ATTACHMENT FOR AN OPTICAL FIBER TO PROVIDE A UNIFORM LEVEL OF ILLUMINATION ACROSS A PLANE

TECHNICAL FIELD

The present invention relates to photodynamic therapy methods and devices. More particularly, the present invention is directed to devices which provide and deliver a highly uniform irradiation beam which is particularly suitable for photodynamic therapy.

BACKGROUND ART

Photodynamic therapy (PDT) exploits the selective uptake of a photosensitizer in tumors and other hyperproliferative target tissues. Since the difference between target tissue uptake of photosensitizer and that of normal tissue is at best only marginal, uniform delivery of light is crucial to attain optimal photodynamic effect. Some degree of selectively may be achieved by simply aiming the light beam at the desired target tissue, but to truly offer selectively of action on target tissue versus adjacent or intermixed normal tissue, selective uptake of dye into target tissue and uniform delivery of light is required. Variations in applied light intensity may result in certain areas within a treatment field receiving over or under dosing. Thus, tumor tissue may be inadvertently spared destruction if present in an area of under treatment, while normal tissue may be destroyed if light intensity is focally increased in a certain area.

Clinical applications of PDT have used free optical fibers as well as diffusing lenses to administer laser light to treatment areas. Light delivery is usually accomplished with an argon-pumped dye laser using a single wavelength of light. This allows for easy calculation of delivered light dose and an estimate of photodynamic effect.

The selective uptake of dihematoporphyrum ether (DHE) and other photosensitizers within tumors, or other rapidly proliferating tissues, is the basis for most of the therapeutic benefit of PDT. Although photodynamic effect may be directed to specific areas by selective placement of the treatment beam, this affords little benefit in treating most diseases over other descriptive modalities. Selective destruction of target tissue over adjacent, or even intermixed, normal tissue depends upon selective uptake of photosensitizer in target tissue as compared to normal tissue. This has been shown to occur with numerous tumors and other proliferative disorders in vivo, with a variety of photosensitizers. Relative differences in the uptake of DHE into target tissue versus skin, have been shown to be 1.08, 1.8, 2.2, 3.9 and 4.2 in various animal models. Although newer photosensitizers such as the phthalocyanines and 5-ALA-induced protoporphyrin IX may result in even higher relative differences in photosensitizer uptake in target tissue, normal tissues still retain significant amount of photosensitizer in most cases.

Tissue DHE content is a function of the administered DHE and its degree of retention within various tissues. Because differences between target tissue DHE content and normal structures is relative and not absolute, uniform light delivery is imperative to ensure destruction of tumors while sparing normal healthy tissue.

DISCLOSURE OF THE INVENTION

It is accordingly one object of the present invention to provide device for producing and delivering a highly uniform irradiation beam of light.

Another object of the present invention is to provide a light delivery device which is particularly useful for photodynamic therapy.

It is a further object of the present invention to provide a device which produces a beam of light which has a highly uniform illumination throughout the entire field thereof.

A further object of the present invention is to produce a photodynamic light delivery device which can be in direct contact with a target situs during use.

A still further object of the present invention is to provide a method of photodynamic therapy wherein a light delivery device which produces a highly uniform beam of light is in direct contact with a target situs during use.

According to these and further objects of the present invention which will become apparent as the description thereof proceeds, the present invention provides a light delivery device which includes:

a hollow spherical shell which defines a cavity therein and includes a diffusive reflective inner surface;

an input aperture formed within the hollow spherical shell for passing a beam of light into the cavity;

a diffusive reflective surface within the cavity which is supported away from the inner surface of the hollow spherical shell and aligned with the input aperture, whereby light which passes through the input aperture into the cavity is reflected off the diffusive reflective surface before reaching the diffusive reflective inner surface of the spherical shell; and an output aperture formed within the hollow spherical shell through which only light that is reflected off the diffusive reflective inner surface exits the hollow spherical shell.

The present invention further provides a method of applying photodynamic therapy to a target situs which involves:

a) providing light delivery device, the light delivery device including:
  a hollow spherical shell which defines a cavity therein and includes a diffusive reflective inner surface,
  an input aperture formed within the hollow spherical shell for passing a beam of light into the cavity,
  a diffusive reflective surface within the cavity which is supported away from the inner surface of the hollow spherical shell and aligned with the input aperture, whereby light which passes through the input aperture into the cavity is reflected off the diffusive reflective surface before reaching the diffusive reflective inner surface of the spherical shell, and
  an output aperture formed within the hollow spherical shell through which only light that is reflected off the diffusive reflective inner surface exits the hollow spherical shell;

b) positioning the output aperture of the light delivery device near a target situs; and c) delivering light into the light delivery device and therethrough to the target situs.

BRIEF DESCRIPTION OF DRAWINGS

The present invention will be described with reference to the attached drawings which are given by way of non-limiting examples only, in which:

FIG. 1b is an exploded schematic diagram of the integrating sphere of FIG. 1a.

BEST MODE FOR CARRYING OUT THE INVENTION

Figure 1A:
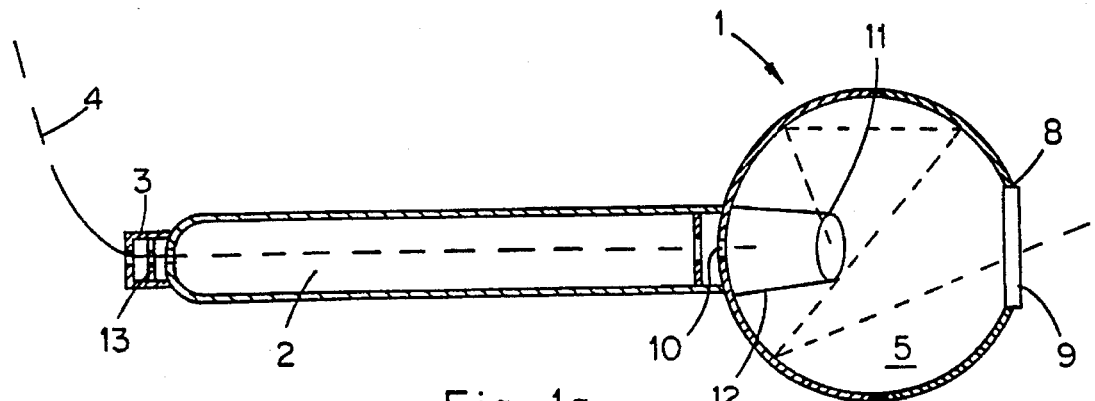
FIG. 1a is a schematic diagram of an integrating sphere according to the present invention.

The present invention is directed to a device which allows for the delivery of a very uniform beam of laser light. The device, referred to herein as an integrating sphere because of its shape, provides exceptional uniform illumination as compared to light output from a diffusing lens and a free optical fiber. The integrating sphere of the present invention is also comparable to a free optical fiber in its ability to produce a uniform eschar on the skin of guinea pigs given dihematoporphyrin ether (DHE). Test results indicate that the integrating sphere of the present invention can allow for optimization of desired effects of PDT, while significantly decreasing over or under dosing problems associated with inhomogeneity of the treatment beam.

The integrating sphere of the present invention provides a simple means of delivering a highly uniform beam of light for use with experimental or clinical PDT. Since, in use, the sphere is placed directly against the tissue to be treated, possible errors in beam height due to patient movement are virtually eliminated. The present invention further decreases problems associated with shielding, while allowing quick and easy application of light by simply applying the device over the desired treatment area. Moreover, the desired photodynamic effect is optimized because of the highly uniform beam of light produced by the device.

The integrating sphere of the present invention includes a handle and a hollow sphere attached to the handle. The handle receives an optical fiber through which laser light is directed into the inside of the hollow sphere. The light enters the hollow sphere and is diffused by and reflected off of a reflector or target supported in the hollow sphere. The reflected light is then internally reflected numerous times off of the inner surface of the hollow sphere which is provided with a diffusive reflective coating. After internally reflecting within the hollow sphere, the light emerges through an aperture formed within the wall of the hollow sphere. The emerging light has high degree of field uniformity resulting from the internal reflection within the hollow sphere.

Tests conducted during the course of the present invention have demonstrated that significant variability in light beam homogeneity may exist with some light delivery systems which are presently being used to administer PDT. Although such delivery systems may be manipulated by changing optical fiber orientation and laser output to attain a more uniform light beam, these manipulations are not consistent. In addition, undesirable changes in light uniformity may occur with movement of optical fibers or changes in laser output characteristics. The integrating sphere of the present invention delivers a uniform beam of light in spite of variabilities in laser output characteristics or changes in laser optical fiber position. In the integrating sphere of the present invention, only the light intensity would change if the output of the laser varied during treatment.

Figure 1B:
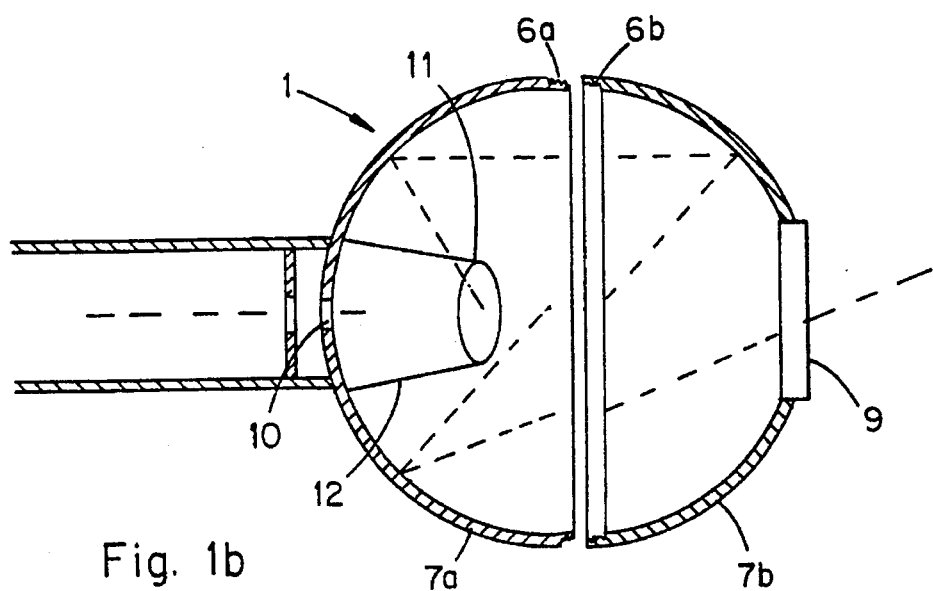

FIG. 1a is a schematic diagram of an integrating sphere according to the present invention. As shown in FIG. 1a the device includes a spherical shell 1, a handle 2, a optical fiber support 3, and a optical fiber 4. The spherical shell 1 has a diffusive reflective inner surface and is preferably made from two half shells (FIG. 1b), which define spherical cavity 5 when attach together. FIG. 1b is an exploded schematic diagram of the integrating sphere of FIG. 1a. As shown in FIG. 1b, the two halves 7a and 7b of the spherical shell 1 are preferably held together by cooperating internal and external threaded portions 6a and 6b which are shown in FIG. 2b. In an alternative embodiment, the spherical shell halves can include flanges in place of the threaded portions 6a and 6b which can be secured together by mechanical fasteners, e.g., screws, bolts, clips, etc. In a further embodiment the threaded portions 6a and 6b could be replaced by a bayonet mounting structure. The two half shells 7a and 7b should be made from a solid material which is sufficiently heat resistant. Metals are preferred. Aluminum is more preferred because of its light weight.

The ability to separate the shell halves 7a and 7b from each other allows for easy cleaning or repair should this be necessary. The distal hemisphere (shell half 7b) of the spherical shell 1 includes an output port 8 through which a treatment beam exits. The output port aperture may be covered with a transparent, e.g., glass, window to prevent dust from entering the spherical cavity 5. The diameter of the output port 8 can be as large as the diameter of the spherical shell 1, or as small as desired for a particular application. The shape of the output port need not be circular. However, a circular output port is suitable for general application. The proximal hemisphere (shell half 7b) is attached to a hollow handle 2. The hollow handle 2 is preferably made from a material which is sufficiently heat resistant. Metals are preferred. Aluminum is more preferred because of its light weight. The proximal hemisphere can be attached to the handle 2 by welding, cementing, epoxying, mechanical means, e.g., threaded connection, or any other suitable means.

At the center of the area of the spherical shell 1 where the handle 2 is attached there is a small aperture 10. As discussed in more detail below, the aperture 10 allows light to enter the spherical cavity 5.

Figure 1C:
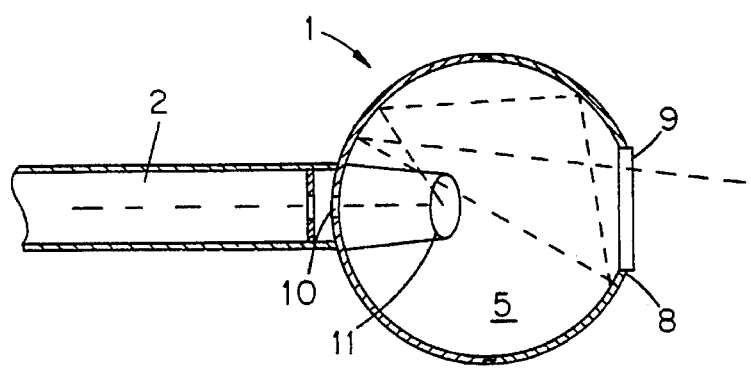
FIG. 1c is an exploded schematic diagram of an integrating sphere according to one embodiment of the present inventor which includes a diffusive reflective surface that is convex.

A reflector or target 11 is located within the spherical cavity 5 and aligned with the aperture 10. The reflector or target 11 is supported away from the aperture 10 by a plurality of supports or stand-offs 12. The reflector or target 11 has a diffusive reflective surface which faces the aperture 10. The diffusive reflective surface of the reflector on target 11 can be planar, or convex. (See FIG. 1c) The distance between the aperture 10 and the reflector or target 11 should be adjusted so that the light entering the spherical shell 1 undergoes a maximum amount of internal reflection. Generally it has been found that the distance between the aperture 10 and reflector or target 11 should be between about one to one-sixth the radius of the spherical shell 1 for a planar diffusive reflective surface and less, e.g. one-tenth to one-half the radius of the spherical shell 1 for a convex diffusive reflective surface. It is to be understood that the reflector or target 11 should be appropriately sized and positioned so as to prevent (i.e., block) light delivered by optical fiber 4 from passing directly through the output port 8. According to a preferred embodiment, the reflector or target 11 is circular.

A optical fiber support 3 is attached to the proximal end of the handle 2. The optical fiber support 3 acts as a connector for optical fiber 4 which is received in and supported by the optical fiber support 3. The optical fiber support 3 includes a through-bore having a gasket or bushing 13 therein, e.g., an O-ring, into which an end of the optical fiber 4 can be inserted. Additional gaskets or bushings can be provided within the handle 2 to receive and support the optical fiber 4 in proper alignment. The optical fiber support 3 can be attached to the end of the handle 2 by welding, cementing, epoxying, mechanical means, e.g., threaded connection, press fit, or any other suitable means. The optical fiber support 3 can be made from any material which is mechanically strong and has a sufficient heat resistance. Metals are preferred. Aluminum is more preferred because of its light weight.

In a preferred embodiment, the optical fiber 4 is held by the optical fiber support 3 so that an end thereof is positioned about half-way between the reflector or target 11 and the wall of the spherical shell 1. The entire inside of the spherical shell 1, the stand-offs 12 and reflector or target 11 are all coated with a diffusive reflective coating. Such a diffusive reflective coating can be applied by any convenient means. According to one embodiment of the present invention, the diffusive reflective coating was applied using an air-brush technique. A preferred diffusive reflective coating found to be useful for purposes of the present invention was a Kodak analytic standard white diffusive reflective coating in an ethanol base (Eastman Kodak Co., Rochester, N.Y.). However, any known diffusive reflective coating material could be used according to the present invention.

All light coming from the integrating sphere's aperture 10 is internally reflected. In use the output port 8 (or window 9 of the integrating) sphere can be placed flush in contact with a target tissue. This eliminates shielding so that only the center of a beam of light is used.

According to the present invention the size of the spherical shell 1 and output port 8 can be chosen as appropriate to treat lesions of different sizes. In this regard, changing from one spherical shell size to another can be easily accomplished by providing a detachable connection between the proximal hemisphere (half shell 7a) of the spherical shell 1 and the handle 2, e.g., a mechanical connection such as a threaded connection, a bayonet mounting structure, a luer lock structure, or the like.

Features and characteristics of the present invention will be illustrated by the following examples to which the present invention is not to be considered limited. In the examples and throughout percentages are by weight unless otherwise indicated.

EXAMPLE 1

In this example, the uniformity of three different delivery devices was tested. Green 514 nm light was delivered using an argon laser (model PRT 100, Coherent Inc., Palo Alto, Calif.) coupled to a 600 micron, fused silica, flat end optical fiber (model PCS 600, Q. P. C., Inc., Plainfield, N.J.). Laser output was measured at the optical fiber tip using a power meter (model 210; Coherent, Inc., Pal Alto, Calif.) resulting in a surface dose rate of 30 mW/cm$^2$.

The light was delivered by three methods: a non-optimized flat-end cleaved optical fiber, a non-optimized 600 μm microlens (Laser Therapeutics, Inc., Buelton, Calif.), and an integrating sphere according to the present invention. Light was delivered in a 1.0 cm diameter circle in the first 2 cases. The integrating sphere used here had a circular aperture with a diameter of 1.0 cm, and delivered light to the test area when placed against the test site.

Light output measurements were taken using a photodiode clamped in place on a movable vice grip. The vice was moved in 0.5 to 1.0 mm increments along the greatest diameter (1.0 cm) of the light field, for each of the three modes of light delivery used. The photodiode was connected to a computer based light monitoring system. The monitoring system produced numerical readouts of field uniformity for each of the three light delivery methods used. All readings were carried out within a few hours of each other in an identical fashion. Numerical results were plotted on a graph for comparison. Measurements were carried out for the integrating sphere just outside of the aperture for comparison with the other readings, and just inside the aperture to duplicate the actual treatment conditions in which the sphere is used.

Figure 2:
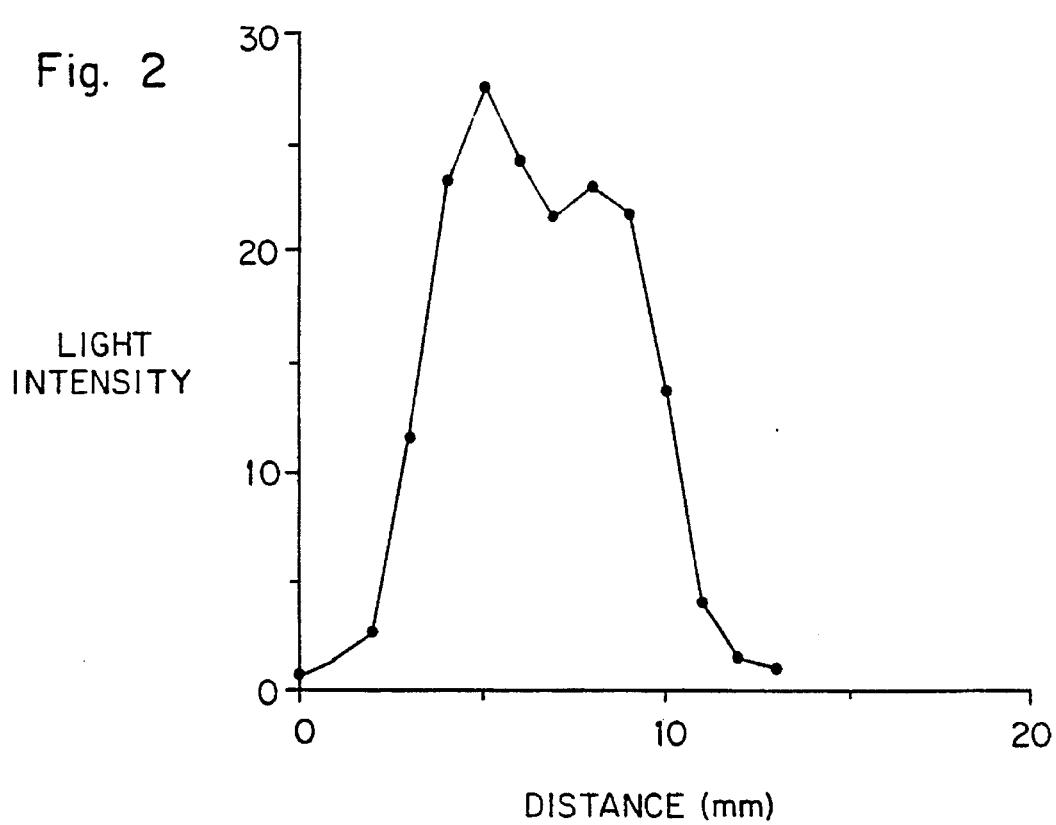
FIG. 2 is a plot of the intensity output of a free cleaved optical fiber.

FIG. 2 is a plot of the intensity output of a free cleaved optical fiber. As seen from FIG. 2, the light output across the 1.0 cm diameter circle produced by the free optical fiber varied significantly across the largest diameter of the field. Across the center 0.4 cm of the 1.0 cm beam, light intensity varied by as much as 21%.

Figure 3:
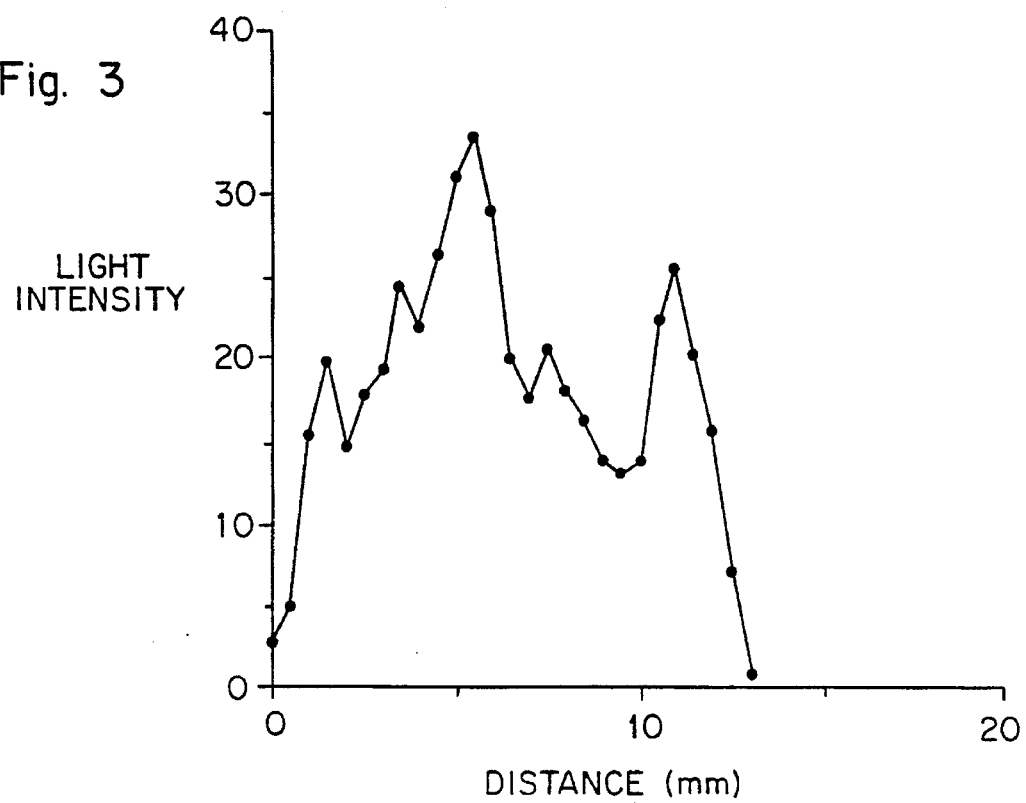
FIG. 3 is a plot of the intensity output of an optical fiber having a diffusing lens on the end thereof.

FIG. 3 is a plot of the intensity output of an optical fiber having the diffusing lens on the end thereof. As seen in FIG. 3, the light output across the 1.0 cm field produced by 600μm microlens also varied significantly across the largest diameter of the field. Across the center 0.4 cm, light intensity varied by more than 60%.

Figure 4:
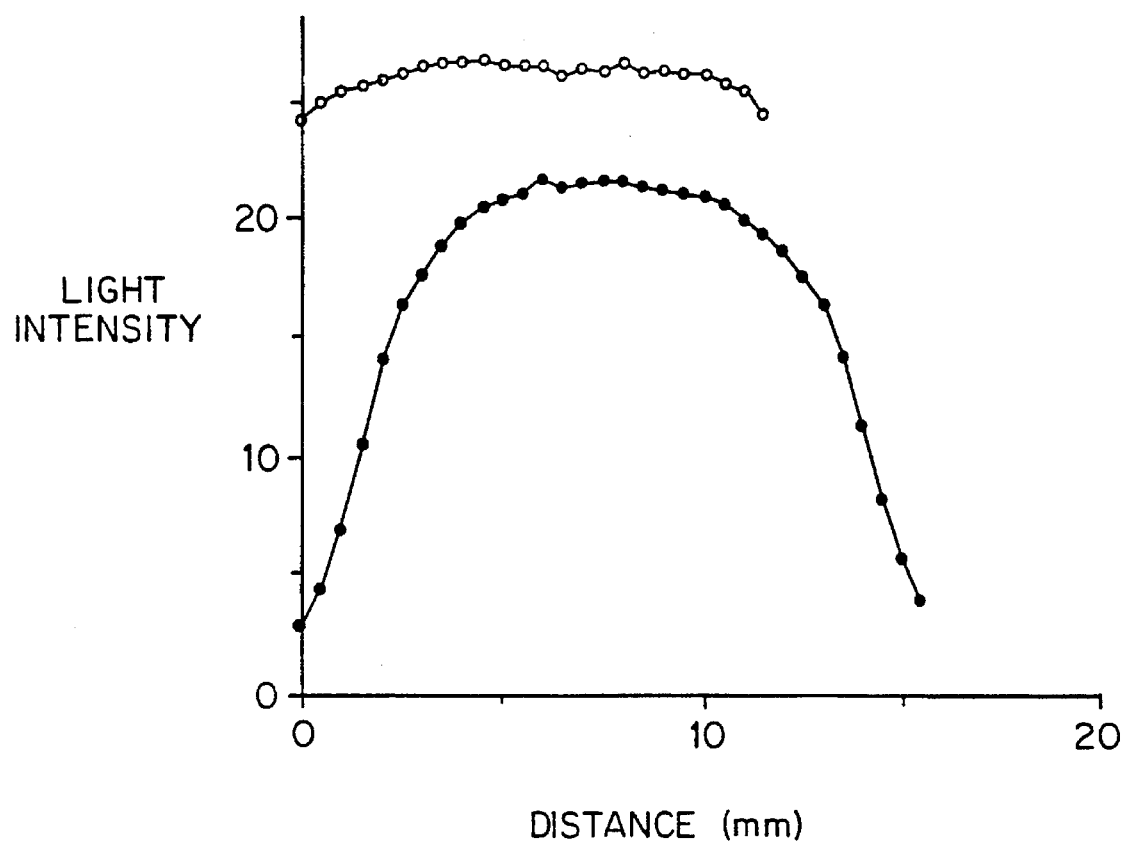
FIG. 4 is a plot of the intensity of the integrating sphere of the present invention measured just outside the aperture (closed circles) and just inside the aperture (open circles).

FIG. 4 is plot of the intensity of the integrating sphere of the present invention measured just outside the output port (closed circles) and just inside the output port (open circles). As seen in FIG. 4, the integrating sphere delivered a highly uniform beam varying by only 4% across the center 0.4 cm of the light beam. When measuring light intensity just within the output port of the sphere, as would be the case when placing the sphere against target tissue, the beam intensity varied by less than 10% over the entire 1.0 cm diameter. Across the center 4.0 mm of this field, light intensity only varied by less than 2%. EXAMPLE 2

In this example, five adult Hartley albino guinea pigs (0.45–0.55 kg) were used for testing purposes. Hair removal was accomplished 24 hours after photosensitizer administration by shaving with animal clippers and subsequent application of a depilatory lotion which was allowed to dry for 15 minutes then was completely removed with warm water. Hair removal was complete with little or no erythema. Depilation was accomplished 24 hours prior to laser light treatments. Hair removal and light treatment were carried out after anesthesia with intraperitoneal ketamine hydrochloride (90 mg/kg) and xylazine (5 mg/kg) administered intraperitoneally. After photosensitizer administration and until the experiments were completed, guinea pigs were housed in reduced lighting and shielded from direct light. Post treatment, guinea pigs were individually housed to prevent them from tampering with each other's treatment sites.

Photofrin II®(Quadra Logics Technologies, Vancouver, British Columbia) brand of dihematoporphyrin ethers (DHE), a purified product of hematoporphyrin derivative (HPD), in an isotonic saline solution at a concentration of 2.5 mg/ml was used as the photosensitizer. Lyophilized DHE was kept in the dark at −70° C. until just before use, and reconstituted with water resulting in an isotonic solution. DHE was administered intraperitoneally at 10 mg/kg two days before laser treatment.

Treatment sites were located on the backs of all guinea pigs in two linear arrays of 3 sites. Each animal had a total of 6 sites treated, 3 on the left side and 3 on the right. Skin surface temperature was monitored throughout treatment.

invention (bottom). Sites treated with the free optical fiber showed increasing areas of eschar as the light dose increased. Guinea pigs receiving light and no DHE showed no evidence of eschar formation at any dose. Temperatures increased by no more than 2.9° C. during treatment.

The relevant data from the tests performed in Example 2 are presented below in Table 1.

TABLE 1

| Light dose | Photodynamic effect of integrating sphere versus free optical fiber on guinea pig skin | | | | | |
|---|---|---|---|---|---|---|
| | Sphere 1 | Fiber 1 | Sphere 2 | Fiber 2 | Sphere 3 | Fiber 3 |
| 10 J/cm$^2$ | 0*(0%)† | .30(38%) | 0(0%) | .15(19%) | 0(0%) | .15(19%) |
| 20 J/cm$^2$ | .86(109%) | .51(65%) | .78(100%) | .64(82%) | .98(125%) | .50(64%) |
| 30 J/cm$^2$ | .86(109%) | .92(124%) | .82(105%) | .95(121%) | 1.0(129%) | .89(114%) |

Light doses of 10, 20, and 30 J/cm$^2$ were delivered to all 3 guinea pigs. Each animal received 3 sites treated to the above doses with an open optical fiber on one side, and with the integrating sphere on the contralateral side. The experiment was repeated in triplicate. All treatment doses were delivered in anatomically identical locations on the left and right sides of each guinea pig After light administration treatment sites were lightly marked in indelible black ink. Two animals were not given photosensitizer, otherwise they were treated in an identical manner.

Treatment sites were evaluated for eschar formation on day 7. This time period was determined to correspond to maximal visible damage. Lesions were only compared with those on a given animal to control for variation in absorption of HPD between animals. Treatment sites were photographed on day 7, with a ruler to allow standardization of treatment sizes. Photographs were then placed in front of a video camera and digitized by a computer. Digitized images were then subject to analysis of eschar size in treatment areas as computed using the digital imaging program. These values were compared to ideal area of illumination which were 1 cm circles in each case. Circles made by the free optical fiber were made to be exactly 1 cm in diameter by adjusting the treatment height of the optical fiber. The integrating sphere had an output port forming a circle 1 cm in diameter, which was placed directly in contact with the skin of each guinea pigs.

Area of eschar as calculated using a computer based graphics system are shown in Table 1. Eschars more closely corresponded with the size of the treatment field when using the integrating sphere than when using the free optical fiber. Eschar sizes were compared to an ideal 1.0 cm$^2$ circle, which has an area of 0.785 cm$^2$. Treatment sites varied from the ideal circle by an average of only 12.8% when treated with the integrating sphere, versus 40.7% with the free optical fiber. Small eschars were produced centrally by the free optical fiber at a light dose of 10J/cm$^2$ with the free optical fiber but not with the integrating sphere. This dose has been shown to be below the threshold for eschar formation in guinea pig skin when using uniform treatment beams. Uniform eschars were produced with the integrating sphere at light dose of 20 and 30 J/cm$^2$.

Figure 5:
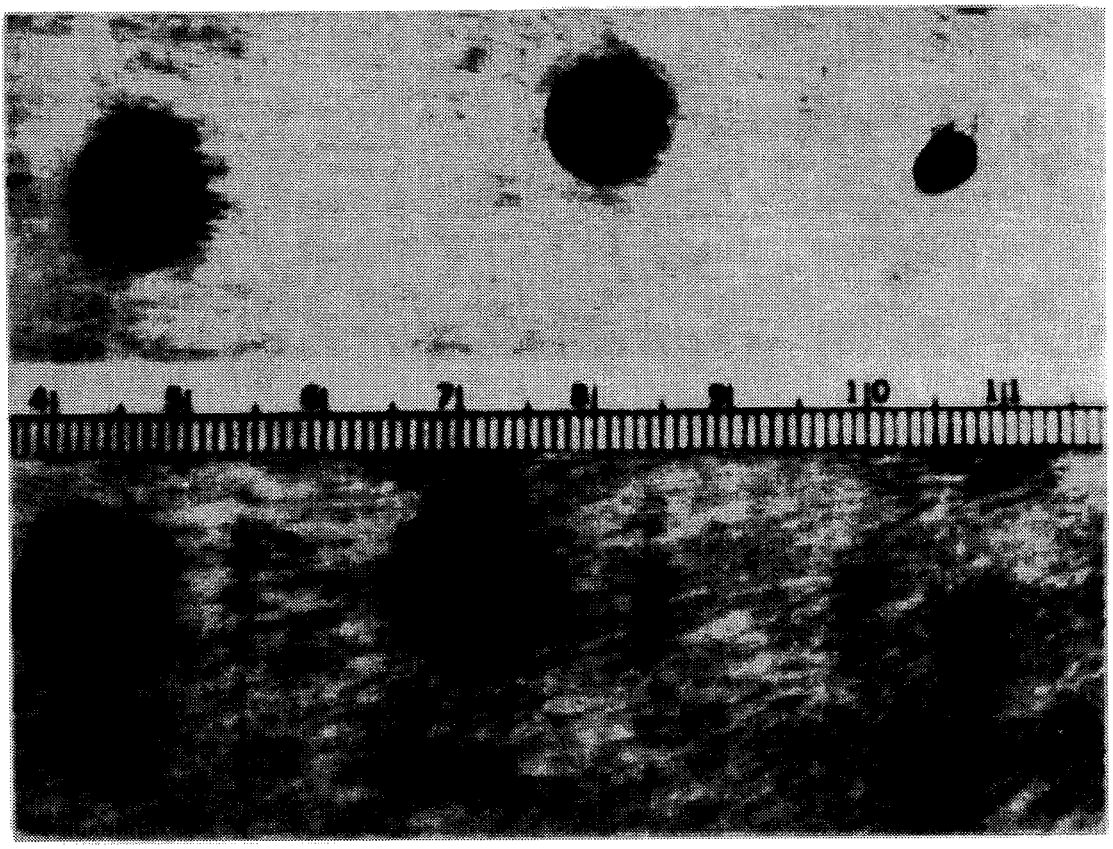
FIG. 5 shows eschars formed on guinea pigs which were given photodynamic therapy utilizing a free optical fiber (top) and an integrating sphere according to the present invention (bottom).

FIG. 5 shows eschars formed on guinea pigs which were given photodynamic therapy utilizing a free optical fiber (top) and an integrating sphere according to the present In Table 1, areas of eschar produced by light administration to guinea pigs given 10 mg/kh DHE, as calculated by computer graphics program are expressed in cm$^2$. Results are paired with designations 1, 2 and 3 referring to treatments done on either side of each of the three guinea pigs. Each guinea pig received a total of six reaction sites: three on the first side using the integrating sphere, and three on the other side using the free optical fiber. "Sphere" refers to the side treated with the integrating sphere and "Fiber" refers to the side treated with the free optical fiber to the light doses shown.

The expected area for a 1 cm diameter circle using $\pi R^2$ is 0.785 cm$^2$. Each area (in parentheses) is expressed as a percentage of this expected value.

From the above, it can be seen that the integrating sphere of the present invention provides a highly uniform illumination beam, which is particularly applicable to photodynamic therapy. In this regard, the present invention further provides additional advantages such as elimination of required shielding, and quick and easy application of light over a desired treatment site. Beyond phototherapy procedures, the integrating sphere of the present invention can be used in any application in which a highly uniform illumination field is required, such as optical examination and imaging.

Although the present invention has been described with reference to particular means, materials and embodiments, from the foregoing description, one skilled in the art can easily ascertain the essential characteristics of the present invention and various changes and modifications may be made to adapt the various uses and characteristics without departing from the spirit and scope of the present invention as described by the claims which follow.

We claim:

1. A light delivery device which comprises:
   a hollow spherical shell which defines an outer spherical surface and a spherical cavity therein, and which includes a diffusive reflective inner surface;
   an input aperture formed within said hollow spherical shell for passing a beam of light into said cavity;
   a diffusive reflective surface within said cavity which is supported away from the inner surface of said hollow spherical shell and aligned with said input aperture, whereby light which passes through said input aperture into said cavity is reflected off said diffusive reflective surface before reaching the diffusive reflective inner surface of said spherical shell;

an output aperture formed within said hollow spherical shell through which only light that is reflected off said diffusive reflective inner surface exits said hollow spherical shell; and a handle which is capable of being detached from said outer spherical surface of said hollow spherical shell at a position which covers said input aperture.

2. A light delivery device according to claim 1, wherein said output aperture is covered by a transparent window.

3. A light delivery device according to claim 1, wherein said input and output apertures are diametrically opposed from one another.

4. A light delivery device according to claim 1, wherein said diffusive reflective surface is supported from said inner surface of said hollow spherical shell by a plurality of supports.

5. A light delivery device according to claim 1, wherein said diffusive reflective surface is planar.

6. A light delivery device according to claim 5, wherein said diffusive reflective surface is supported away from the inner surface of said hollow spherical shell by a distance which is between about one to one-sixth a radius of said hollow spherical shell.

7. A light delivery device according to claim 1, wherein said diffusive reflective surface is convex.

8. A light delivery device according to claim 7, wherein said diffusive reflective surface is supported away from the inner surface of said hollow spherical shell by a distance which is between about one-tenth to one-half a radius of said hollow spherical shell.

9. A light delivery device according to claim 1, wherein said hollow spherical shell comprises two half shell portions which are connected together.

10. A light delivery device according to claim 9, wherein said two half shell portions included cooperating threaded portion by which said two half shell portions can be connected together.

11. A light delivery device according to claim 1, wherein said handle is hollow.

12. A light delivery device according to claim 11, wherein an optical fiber support is connected to said handle.

13. A light delivery device according to claim 12, wherein said optical fiber support is connected to said handle at an end thereof which is opposed to said hollow spherical shell.

14. A light delivery device according to claim 12, wherein said optical fiber support includes a gasket means for receiving and securing an optical fiber.

15. A light delivery device according to claim 1, wherein said hollow spherical shell is made from a metal and said diffusive reflective inner surface of said hollow spherical shell comprises a diffusive reflective coating.

16. A method of applying photodynamic therapy to a target situs which comprises:

a) providing light delivery device, said light delivery device including:

a hollow sperical shell which defines an outer sperical surface and a sperical cavity therein, and which includes a diffusive reflective inner surface, an input aperture formed within said hollow sperical shell for passing a beam of light into said cavity, a diffusive reflective surface within said cavity which is supported away from the inner surface of said hollow spherical shell and aligned with said input aperture, whereby light which passes through said input aperture into said cavity is reflected off said diffusive reflective surface before reaching the diffusive reflective inner surface of said spherical shell, an output aperture formed within said hollow spherical shell through which only light that is reflected off said diffusive reflective inner surface exits said hollow spherical shell, and a handle which is capable of being detached from said outer spherical surface of said hollow spherical shell at a position which covers said input aperture;

b) positioning said output aperture of said light delivery device near a target situs; and c) delivering light into said light delivery device and therethrough to said target situs.

17. A method of applying photodynamic therapy to a target situs according to claim 16, further comprising providing the output aperture with a transparent window and placing said transparent window near the target situs in step b).

18. A method of applying photodynamic therapy to a target situs according to claim 17, wherein said window is placed against the target situs in step b).

* * * * *